United States Patent [19]

Couch

[11] Patent Number: 4,528,844
[45] Date of Patent: Jul. 16, 1985

[54] STALL/DEBRIS DISCRIMINATING IONIC ENGINE DIAGNOSTICS

[75] Inventor: Robert P. Couch, Palm Beach Gardens, Fla.

[73] Assignee: United Technologies Corporation, Hartford, Conn.

[21] Appl. No.: 454,112

[22] Filed: Dec. 28, 1982

[51] Int. Cl.³ .......................................... G01M 15/00
[52] U.S. Cl. ........................................ 73/116; 73/115
[58] Field of Search ................. 73/115, 116; 324/459, 324/464; 60/39.03; 340/60

[56] References Cited

U.S. PATENT DOCUMENTS 3,469,398  5/1967  Schafer ........................... 324/464 X
3,513,692  5/1970  Slone ................................... 73/116
4,359,893  11/1982  Kizler .............................. 73/116 X Primary Examiner—John W. Caldwell, Sr.
Assistant Examiner—Ellwood G. Harding, Jr.
Attorney, Agent, or Firm—M. P. Williams; Gerald E. Linden

[57] ABSTRACT

A pair of biased electrostatic probes (27a, 28a) disposed directly within respective dilution air inlets (32) of the combustor (20) in a gas turbine engine (10) provide an indication (62, 68) of surge/stall in response to the outflow of ionic combustion products from the burner can, and block (120, 122, 128) signals (129), indicative of charged engine debris, from reaching wear monitor signal processing apparatus (134).

2 Claims, 5 Drawing Figures

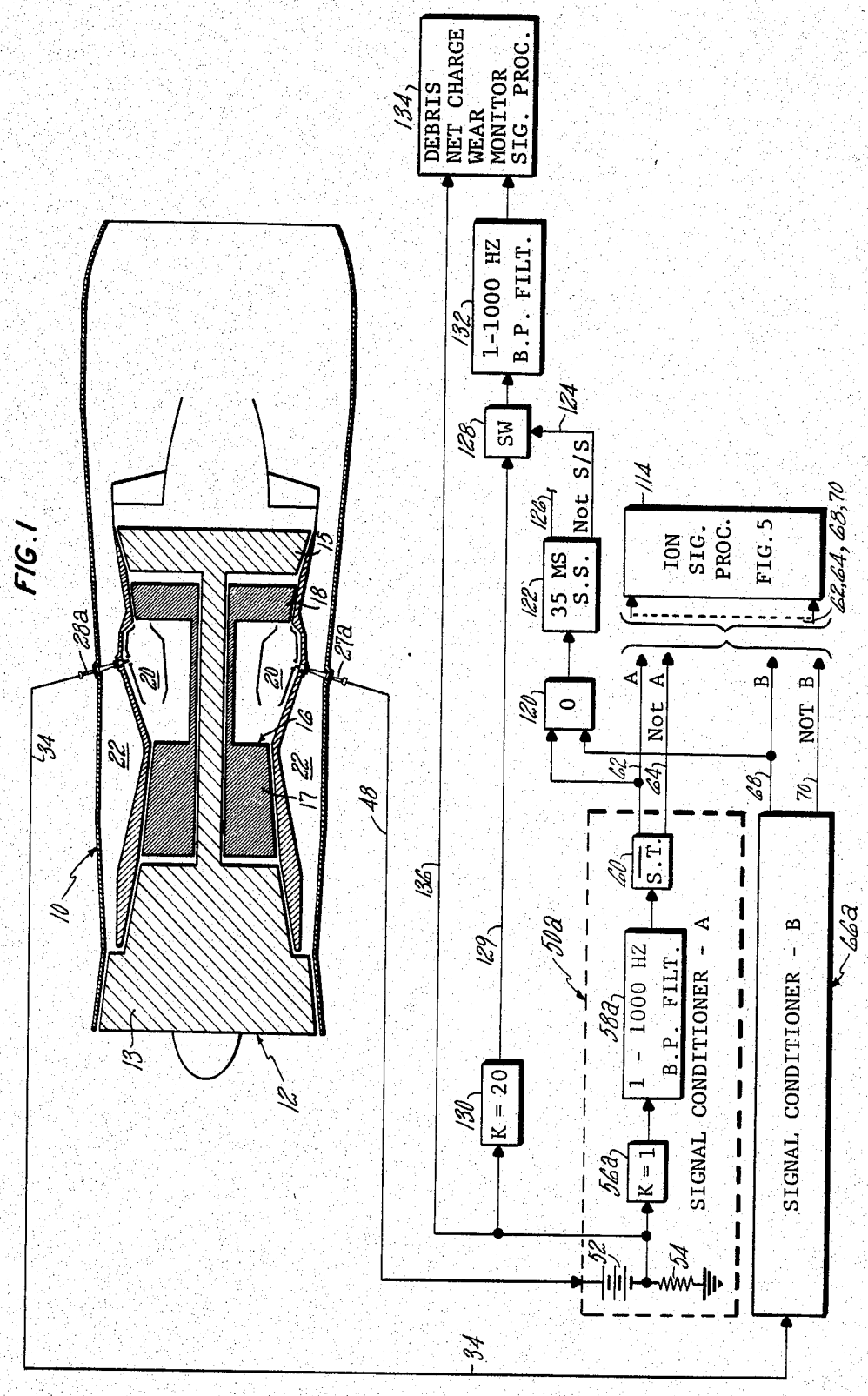

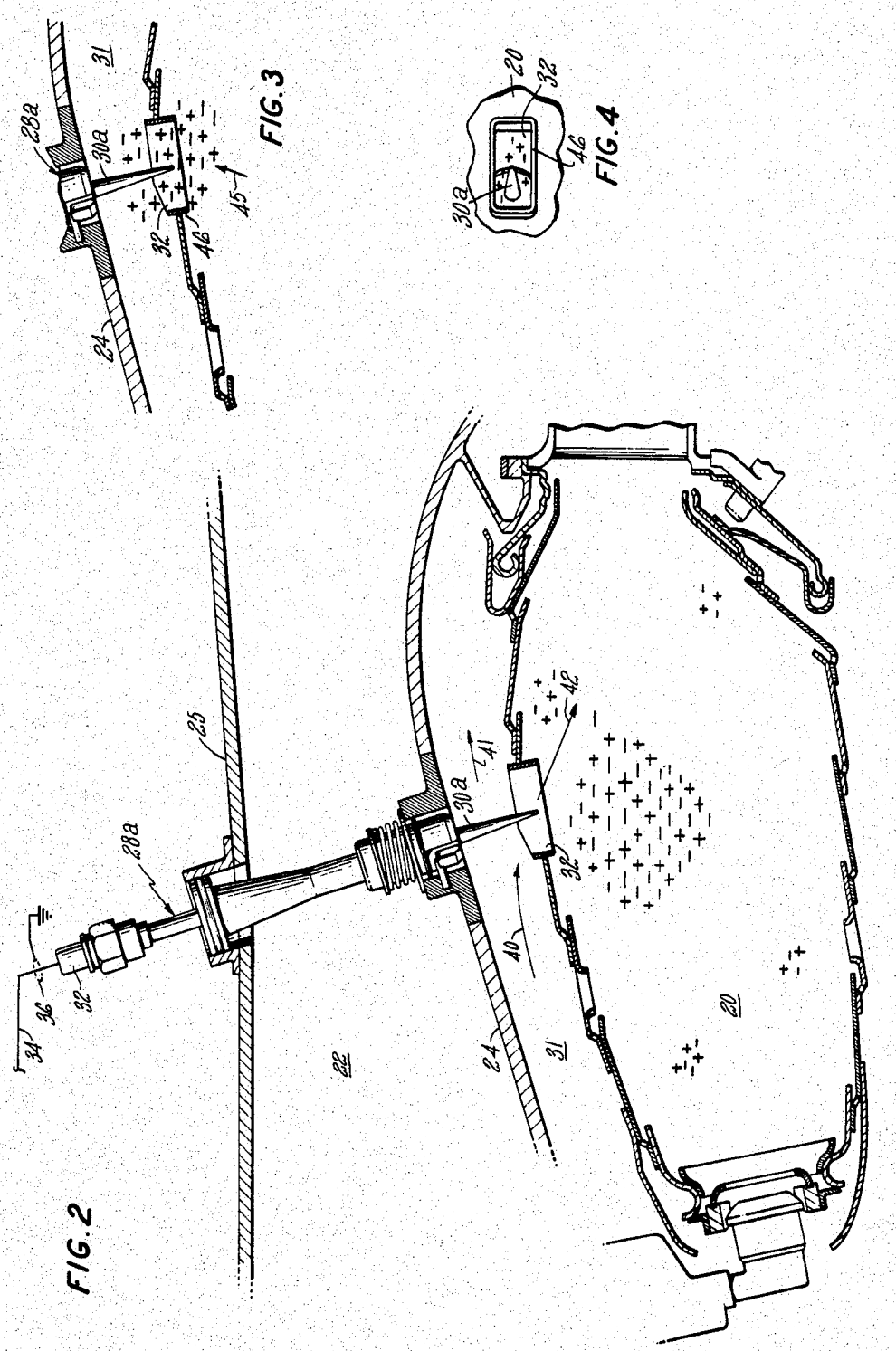

STALL/DEBRIS DISCRIMINATING IONIC ENGINE DIAGNOSTICS

DESCRIPTION

1. Technical Field

This invention relates to surge/stall detection in gas turbine engines, and more particularly to early detection of surge/stall and discrimination between surge/stall and electrostatic debris indicative of engine wear.

2. Background Art

As is known in the gas turbine art, compressor surge can occur as a consequence of stall conditions on a sufficient number of compressor blades. Blade stall is known to result from various, conditions, including: severe acceleration (variously referred to as "jam" or "bodie"); during sideslip or skid (when in evasive action) or as a consequence of turbulent air, which upset conditions at the engine air inlet; or from a violent afterburner light-off. These perturbations cause a sufficient change in the velocity of gas flow through the engine in contrast with the rotational velocity of the compressor blades, for a given compressor blade angle, so that the resultant angle of attack causes airfoil stall. When a sufficient number of blades are stalled, a surge (a detectable, violent engine event) may occur. A mild surge may simply result in a momentary pressure drop and flow reversal of the gas stream which is self-recoverable. A more severe surge may result in multiple surge cycles which may be self-recoverable or may require control action to assist recovery. Under certain conditions, surges can result in rotating stall and airflow stagnation, in which the stall condition has so upset the compression process that sufficient energy for recovery is not available without some external action being taken.

In some engines, stall conditions vary significantly, and can cause different results. For instance, blade stall may result in a surge or a rotating stall stagnation condition. A rotating stall stagnation is characterized by normal gas flow and combustion at some sectors of the engine and abnormal gas flow and combustion at another sector of the engine, the circumferential position of the abnormal sector rotating less than half the engine rotational speed. The net result is abnormally low airflow which is insufficient to sustain compressor speed.

In a commonly owned, copending U.S. patent application entitled "Electrostatic Gas Turbine Surge/Stall Detection", U.S. Ser. No. 454,121, filed contemporaneously herewith by St. Jacques et al, a surge/stall detector senses the presence of ionic combustion products in a compressor outflow duct feeding the combustor or burner can of a gas turbine engine. Therein, a voltage-biased electrostatic probe is disposed adjacent a dilution air inlet of a gas turbine engine combustor, reverse flow through the dilution air inlet causing highly ionic flame and combustion products in the region of the electrostatic probe, resulting in conductivity from the probe to the combustor and other engine walls, thereby providing an electric signal indicative of reverse gas flow in the engine (surge/stall).

A commonly owned, copending U.S. patent application entitled "Waveform Discriminated Electrostatic Engine Diagnostics", U.S. Ser. No. 454,124, filed contemporaneously herewith by Zwicke et al, discloses the correlation between particular events in the engine, some of which are related to specific types of engine deterioration, with the wave shapes of electrical signals generated by electrostatic charge in the engine gas stream. The electrostatic charge indicative of engine wear, and other occurrences in the engine, is believed to be clusters (pockets or boluses) of net charge resulting from rubbing of engine parts or erosion (high temperature corrosion) of engine parts. This is in contrast to conduction through ionic combustion products of the aforementioned St. Jacques et al application, which has no net charge. In the utilization of wear monitor apparatus of the type disclosed in the aforementioned Zwicke et al application, the occurrence of surge/stall phenomena produces significant net charge effects, particularly with respect to a probe disposed in the vicinity of the burner can, as is the case in the apparatus of both of the aforementioned applications. In a normal engine (one not exhibiting excessive wear or impending failure) there is a certain amount of net charge electrostatic activity. For instance, there is a generally-constant random electrostatic noise, the magnitude of which varies from engine to engine and also varies with engine power level in any given engine. In addition, an occasional rub or erosion at various parts in the engine can cause distinct pockets of charge in the gas stream of the engine. Therefore, the apparatus of the aforementioned Zwicke et al application records electrostatic events of a significant magnitude (such as four times R.M.S. noise, or the like) but analyzes the results to determine the causal connection between an excessive number of electrostatic events and engine wear only following an abnormal amount of electrostatic activity. For instance, the activity may be classified for correlation with engine wear only when ten times the normal amount of events occur within a given time frame which is usually related to the amount of work being performed by the engine.

Because simple surges can occur on a random basis in even healthy engines (particularly in high performance engines where air inlet perturbations and the like can disturb the pressure/flow patterns of the engine), wear monitor apparatus of the type disclosed in the aformentioned Zwicke et al application may frequently be analyzing large volumes of electrostatic wear data which are indicative only of normal surge conditions. This clutters the record and tends to mask the presence of wear events of interest, particularly where trending is involved.

DISCLOSURE OF INVENTION

Objects of the invention include provision of a maximally sensitive ionic surge/stall detector for a gas turbine engine, and provision of discrimination between debris net charge indicative of engine wear and ionic conduction indicative of surge/stall in gas turbine engine ionic/electrostatic engine monitoring.

According to the present invention, a voltage-biased electrostatic probe is disposed directly within a dilution air inlet of a gas turbine engine combustor so that perturbation of normally-inward gas stream flow through the dilution air inlet provides highly ionic combustion products within the dilution air inlet, resulting in conductivity from the probe directly to the combustor walls at the dilution air inlet thereby providing an electric signal through said probe of a significant magnitude. According further to the present invention, an electric signal developed in response to current through a biased electrostatic probe, disposed directly within the dilution air inlet hole of a gas turbine engine combustor, in response to perturbation of gas stream flow into the combustor, is a full order of magnitude greater than the signal developed thereby in the case where the probe is disposed adjacent to the dilution air inlet, as in the aforementioned St. Jacques et al application. In further accord with the present invention, a voltage biased electrostatic probe disposed directly within a dilution air inlet hole of a gas turbine combustor is utilized both for debris net charge engine wear monitoring and for surge/stall detection, the detection of surge/stall disconnecting the probe from the input of wear monitor signal processing apparatus. According further to the present invention, an electric signal developed in response to current through a biased electrostatic probe, disposed directly within the dilution air inlet hole of a gas turbine engine combustor, in response to perturbation of gas stream flow into the combustor, is a full order of magnitude greater than the signal developed thereby in response to debris net charge in the gas stream of the engine resulting from engine wear.

The present invention, by providing a probe signal indicative of surge/stall which is an order of magnitude larger than signals which result from wear-indicating pockets of charge flowing in the gas stream of the engine, permits continuous monitoring for both surge/stall and engine debris, the surge/stall signal processing equipment being insensitive to engine debris net charge, so that surge/stall indications can be utilized to disconnect the engine wear monitor signal processing apparatus from the probe.

The present invention may be utilized in a simple fashion, or with surge/stall stagnation discrimination of the type described in the aforementioned St. Jacques et al application. The invention may be utilized with complex waveform diagnostics of the type described in the aforementioned Zwicke et al application, or it may be used in conjunction with simpler diagnostic apparatus, such as that described in a commonly owned, copending U.S. patent application entitled "Interprobe Electrostatic Engine Diagnostics Correlation", U.S. Ser. No. 453,964, filed contemporaneously herewith by Rosenbush et al, or of the type disclosed in a commonly owned copending U.S. patent application entitled "Sectional Distress Isolating Electrostatic Engine Diagnostics", U.S. Ser. No. 454,115, filed contemporaneously herewith by Couch. The simplest aspect of the present invention, providing a maximally sensitive surge/stall detector, may also be used to advantage in electrostatic engine diagnostic apparatus having a complex response to events within and around the engine, as disclosed in a commonly owned, copending U.S. patent application entitled "Adaptive Electrostatic Engine Diagnostics", U.S. Ser. No. 454,125, filed contemporaneously herewith by Rosenbush et al. The disclosures of the wear monitor signal processing apparatus in the aforementioned applications are hereby incorporated herein by reference.

The invention may be implemented with a variety of apparatus utilizing techniques and hardware which are readily available to those in the art, in the light of the teachings which follow hereinafter.

Other objects, features and advantages of the present invention will become more apparent in the light of the following detailed description of exemplary embodiments thereof, as illustrated in the accompanying drawings.

BRIEF DESCRIPTION OF DRAWINGS

FIG. 1 is a simplified, schematic block diagram of an exemplary embodiment of the invention employing two probes displaced 180° from each other about an engine;

FIG. 2 is a partial, sectioned side elevation view of a burner can with a probe disposed directly within the dilution air inlet thereof in accordance with the invention, illustrating the flow of gas into the burner can during normal operation of the engine;

FIG. 3 is a simplified, schematic illustration of the burner can and probe of FIG. 2, illustrating the presence of ionic combustion products in the dilution air inlet during surge or stall;

FIG. 4 is a partial plan view of the burner can dilution air inlet, illustrating ionic conduction directly from the probe to the walls thereof.

BEST MODE FOR CARRYING OUT THE INVENTION

Figure 5:
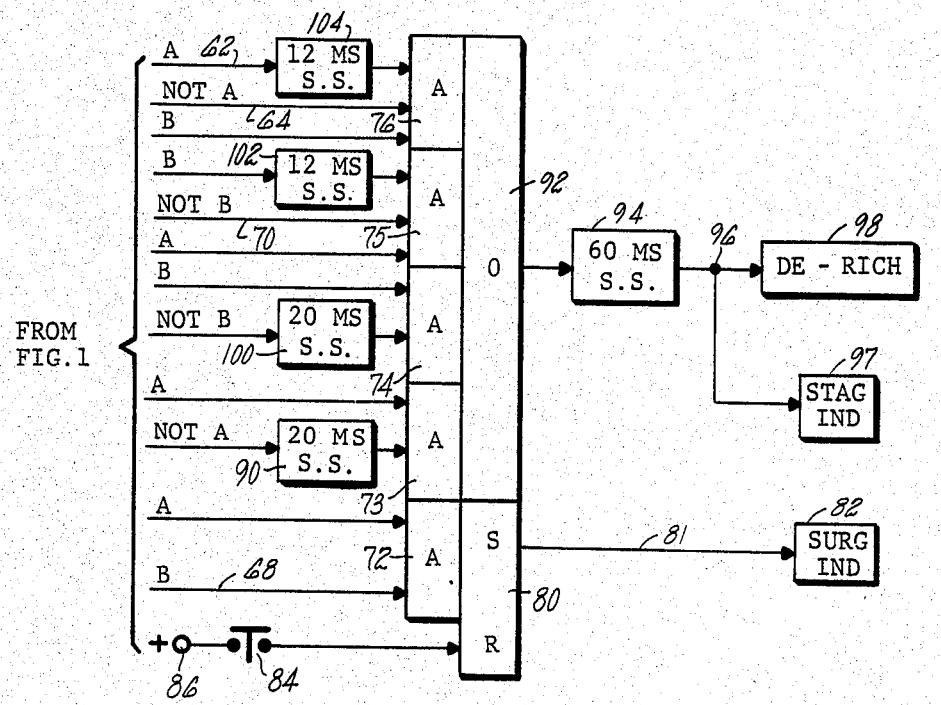
FIG. 5 is a simplified, schematic block diagram of exemplary ion signal processing apparatus of the type described in the aforementioned St. Jacques et al application.

Referring now to FIG. 1, a gas turbine jet engine 10 includes: a low pressure spool 12 having a fan 13, a low pressure compressor 14, and a low pressure turbine 15; as well as a high pressure spool 16, including a high pressure compressor 17 and a high pressure turbine 18. An annular burner can or combustor 20 is disposed between the compressors and the turbines. An annular fan duct 22 is defined by inner and outer annular walls thereof 24, 25, respectively. A pair of probes, 27a, 28a are disposed through the fan duct 22 with their tips in the walls of the burner can 20, as described more fully with respect to FIG. 2.

In FIG. 2, the probe 28a is seen to have an electrode 30a disposed at the burner can 20, and more particularly through a compressor duct passage 31 and with the tip thereof directly within a dilution air inlet 32 thereof. The electrode 30a is insulated from the remainder of the probe 28 and terminates in a connector 32 which joins the electrode to a suitable lead 34, which may preferably comprise the inner conductor of a coaxial cable that includes an external grounded shield 36.

The principal of the invention is illustrated by comparison of FIG. 2 with FIG. 3. In FIG. 2, normal engine operation is illustrated with the flow of dilution air being downstream in the passage 31 between the inner fan wall 24 and the burner can 20, as illustrated by a pair of arrows 40, 41. A significant portion of air passes into the burner can 20 through the dilution air inlet 32, as indicated by the arrow 42. During normal operation, with the flow into the burner can, all of the combustion products remain within the burner can 20 (rather than flowing outwardly in the dilution air inlet 32). The combustion products are highly ionized, as illustrated by the plus and minus signs within the burner can 20 in FIG. 2. On the other hand, whenever blade stall results in surge or stall stagnation, the attendant perturbed pressure condition causes combustion products to flow into the dilution air inlet 32 as illustrated by an arrow 45 in FIG. 3, and may in fact flow upstream in the passage 31 between the fan duct inner wall 24 and the burner can 20; but the invention does not rely on ions in the passage 31. When the combustion products flow into the dilution air inlet 32, as indicated by the plus and minus signs in FIG. 3 and in FIG. 4, the highly ionic gas permits electrical conduction from the probe 30a directly to the walls 46 of the dilution air inlet 32. Thus, a very short path of ion conduction is utilized, and the signal which results is a full order of magnitude greater than that of the St. Jacques et al application.

Referring to FIG. 1, the probe 27a is connected by a conductor 48 (similar to the conductor 34 for the probe 28a) to a signal conditioner 50 for probe A. Within the signal conditioner, the conductor 48 is connected to the positive side of a D.C. source 52, which may be a battery or other suitable power supply, and may have a potential of on the order of 67 volts. The other side of the source 52 is connected through a resistor 54 to ground. When ions are present in the dilution air inlet 32 (FIG. 3 and FIG. 4), current flows from ground through the resistor 54 and battery 52, through the probe 27a (28a), through the ionic plasma in the air inlet 32 and to the walls 46 of the inlet. This provides a voltage on the resistor 54 which may be amplified by an amplifier 56, which may have a gain of about one in contrast with the gain of ten in the St. Jacques et al application. The amplifier output is applied to a band-pass filter 58 which may have a pass band on the order of 1 to 1000 Hz. The filtered signal is applied to a Schmidt trigger 60 having a suitable negative threshold, so that when the input thereto exceeds the negative threshold, a discrete signal, "A", will appear on a line 62. For simplicity herein, it is assumed that the Schmidt trigger 60 is of the type that otherwise provides a discrete signal, "NOT A", on a line 64. Assuming that the battery 52 has a potential of 67 volts, the resistor 54 is 100 kilohms and the amplifier 56 has a gain of about one, the Schmidt trigger may have a negative threshold of about −1 volt. The lead 34 for the probe 28 is connected to a signal conditioner 66 for probe B (which is the same as the signal conditioner 50) that provides B and NOT B signals on lines 68, 70, respectively.

Since surge results from choking at the high pressure end of the compressors, burner pressure normally is rising as the propensity for surge increases. At the onset of the surge, burner pressure begins to drop and may drop from on the order of 50 psia to on the order of 20 psia in about 30 milliseconds (depending upon the severity of the surge and the rotary speed of the engine at the time of surge). After only a few psia drop in burner pressure, reverse flow begins causing the conductivity illustrated in FIG. 3 and FIG. 4 to result in signals through both probe A and probe B on lines 62 and 68, respectively, within 8 or 10 milliseconds of the onset of burner pressure drop. As described in detail in the aforementioned St. Jacques et al application, in the case of an engine having an annular combustor or burner can 20, a severe surge can result in rotating stall stagnation in which, at any given point in time, stall stagnation exists in one sector of the engine, whereas proper combustion, pressure relationships and normal flow conditions exist in other, circumferentially displaced sectors of the engine, the portion of the engine exhibiting stall stagnation rotating about the engine at approximately 40% of engine rotary speed. In a typical case, this amounts to about 16 milliseconds per revolution of the stall stagnation. Since probe A and probe B are displaced from each other, and since the effects of stall stagnation are rotating, the ionic outflow from the burner can (FIG. 3) will reach probe A and then probe B on a 180° phase displacement. This amounts to about 8 milliseconds difference between the time the rotating stall stagnation will be in the vicinity of each of the probes. The rotating stall stagnation can be detected by comparing the phase of signals on the two probes, in on the order of 20 milliseconds from the onset of burner pressure drop. On the other hand, assuming that only one probe were attached to the engine, the cyclic nature of the signals on either of the probes allows detection of stall stagnation by successive pulses on the same probe separated by approximately the period of stall stagnation rotation (here indicated as being about 16 milliseconds). Thus, stall stagnation can not only be detected, but discriminated from surge, by either one probe or two probes in dependence upon whether frequency or phase is utilized to confirm the stall stagnation.

The surge/stall stagnation discrimination is performed in the ion signal processor 114 of FIG. 1, as described herein with respect to FIG. 5. Referring to FIG. 5, the A, NOT A, B, and NOT B signals are utilized, with certain delays, as inputs to a plurality of AND circuits 72-76 to detect and/or distinguish the conditions described above, and to provide respective time signals indicative of the relative times of the signals on the probes. Specifically, an AND circuit 72 detects the simultaneous presence of signals on both probe A and probe B so as to set a bistable device 80 which provides a surge signal on a line 81 to a surge indicator 82, or such other utilization device as may be desired. As shown in FIG. 5, the bistable device 80 may remain set until reset by an operator controlled reset switch 84 which is connected from a suitable source 86 to the reset side of the bistable device 80. On the other hand, the output of the AND circuit 72 may be used in any desired way, as an indication of surge.

The AND circuits 73-76 sense rotating stall stagnation, regardless of the direction of rotation thereof (clockwise or counterclockwise) within the engine 10, and sense it both by phase relationship between probe A and probe B as well as frequency content of the signal on either probe A or probe B, alone. The AND circuit 73 is responsive to a 20 millisecond single shot 90 which provides a signal for 20 milliseconds following the onset of the NOT A signal, which is contemporaneous with the turn-off of the A signal. The AND circuit is also responsive to the A signal. This means that the AND circuit 73 will operate an OR circuit 92 whenever the A signal appears within 20 milliseconds of having previously disappeared. When the OR circuit 92 operates, it will trigger a 60 millisecond single, shot 94, the output of which on the line 96 may be provided to a stagnation indicator 97. It may also be provided to suitable corrective action apparatus, such as a de-rich control 98. In a similar fashion, the AND circuit 74 is responsive to a 20 millisecond single shot 100 connected to the NOT B signal and is also connected directly to the B signal, so that the AND circuit 74 will operate the OR circuit 92 anytime the B signal appears within 20 milliseconds after it has last disappeared. Thus the AND circuits 73, 74 sense the frequency of either the A probe signal or the B probe signal, alone, to detect rotating stall stagnation.

The AND circuits 75 and 76 compare the phase of the A and B signals. The AND circuit 75 is responsive to the A signal concurrently with the NOT B signal, concurrently with the output of a 12 millisecond single shot 102 which provides an output for 12 milliseconds after the appearance of the B signal. Therefore, if the A signal comes up when the B signal is not present, but within 12 milliseconds of the B signal having been present, this senses the 180° phase relationship of FIG. 5 and the AND circuit 75 will cause the OR circuit 92 to operate, thus providing a signal indicative of rotating stall stagnation. Similarly, the AND circuit 76 is responsive to the presence of the B signal when the A signal is absent, but has previously been present within 12 milliseconds, as indicated by the output of a 12 millisecond single shot 104. The utilization of the surge and rotating stall stagnation signals provided by the circuitry of FIG. 5 is not germane to the present invention; any desired utilization of these signals may be made, depending on the manner in which the present invention is used. The invention may be used in conjunction with a single probe, with or without discrimination of surge from stall stagnation, if desired.

The foregoing description of a two-probe surge/stall stagnation detection and discrimination apparatus is essentially the same as that in the aforementioned St. Jacques et al application, with the exception of the details of ionic conductivity in FIGS. 3 and 4 and with respect to those elements described which bear a reference numeral with a suffix, "a". The particular surge/stall stagnation detection and discrimination circuitry is not germane to the present invention, nor is the use to which signals derived thereby may be put. The portion of the description thus far relative to the principal aspect of the invention is that concerning the placement of the electrode tip directly within the dilution air inlet of the burner can (as described in FIGS. 2-4) so as to provide an order of magnitude improvement in the signal obtained thereby, thus to discriminate, by an order of magnitude surge/stall signals from engine debris net charge signals indicative of engine wear.

Referring again to FIG. 1, a simplified embodiment of the second aspect of the present invention includes an OR circuit 120 connected for response to either the A signal on the line 62 or the B signal on the line 68, presence of either one of which will cause the OR circuit 120 to operate a 35 millisecond single shot 122. In the present embodiment, it is assumed that the single shot 122 is of the type which provides a signal on a line 124 when it is in a stable, quiescent condition; But when it receives an input (such as from the OR circuit 120), it provides, instead, a signal on a line 126 (not used herein) for 35 milliseconds following the receipt of an input signal. Therefore, the signal on the line 124 is utilized herein as a not-surge/stall signal. This is used to normally enable an electronic switch 128, which may be an F.E.T. or other suitable transistor switch. The switch 128 normally connects the output on a line 129 of an amplifier 130, which has a gain on the order of twenty times more than the gain of the amplifier 56a, to a bandpass filter 132, which may have a pass band of about 1 to 1000 Hz. The filter in turn is connected to debris net charge wear monitor signal processing apparatus 134. The apparatus 134 may also directly utilize the probe signal developed across the resistor 54 and provided thereto on a line 136. The principal of the second aspect of the invention is that, the pockets of net charge which may flow in the gas stream past the probe 27a within the passage 31 (FIG. 2) are amplified with a gain on the order of 20 in the amplifier 130, and thereby provide useful signals to the wear monitor signal processor 134. But these same charges produce insufficient signals through the amplifier 56a to trip the Schmidt trigger 60. Thus, the ion signal processor 114 is totally insensitive to the presence of charged debris flowing in the engine. On the other hand, the invention is so sensitive to the presence of ionic combustion products within the dilution air inlet that it immediately provides either the A signal on line 62 or the B signal on line 68, or both. This causes opening of the switch 128 thereby cutting off any signal which may have been provided by the amplifier 130 to the wear monitor signal processor 134. Even though the wear monitor signal processor 134 may respond initially to an extremely large signal output from the amplifier 130, it will be cut off so quickly that cluttering the record with repetitive unnecessary indications of surge/stall is avoided. In use of a biased probe shaped and disposed as described in the aforementioned St. Jacques et al application, signals of about 6 microamps are achieved (on the order of one-tenth of a microamp per volt of bias), resulting in raw signals at the resistor 54 of on the order of six-tenths of a volt or so. When amplified by a gain of 10, this results in signals on the order of 6 volts. This has been found to be in the same order of magnitude (2–5 volts) as signals of interest resulting from engine wear debris. In contrast, the present invention provides raw signals of about 60 microamps, thus allowing use of an amplifier 56a of sufficiently low gain that it provides an insignificant output in response to charged debris. It is thus that the sensitivity of the probe shaped and disposed in accordance with the present invention allows amplitude discrimination between surge/stall and engine wear debris. The invention is not concerned with the particular nature of wear monitor signal processor 134 which is utilized; it suffices that this aspect of the invention is satisfied if two signal paths are provided from a sufficiently sensitive, biased electrostatic probe so that one signal path can provide a meaningful signal with a gain an order of magnitude less than a second signal path, and a signal in the first signal path can open up the second signal path.

The exemplary embodiment of the invention shown in FIG. 1 employs analog and logic circuits to discriminate between surge/stall and charged engine debris. The invention may be implemented by means of suitable program routines in a computer or other signal processing apparatus, which program routines are readily implemented with techniques known in the art to sample the signals of the two signal paths and immunize the wear monitor from such signals when they are indicative of surge/stall.

The utilization of the rotating stall indication may include reducing fuel (de-rich), opening compressor bleed valves, water injection, or other corrective action known to the art. The probes 27a, 28a may take the form of any suitable electrostatic probe known to the art, or they may be of the form described in a commonly owned, copending U.S. patent application entitled "Gas Turbine Access Port Plug Electrostatic Probe", U.S. Ser. No. 454,113, filed contemporaneously herewith by Shattuck et al.

Although the invention has been shown and described with respect to exemplary embodiments thereof, it should be understood by those skilled in the art that the foregoing and various other changes, omissions and additions may be made therein and thereto, without departing from the spirit and the scope of the invention.

I claim:

1. Electrostatic responsive apparatus for detecting flow reversal in a gas turbine engine having a compressor, a burner section including a burner can with a dilution air inlet through the walls thereof for allowing compressor outflow to enter said burner can, a compressor duct for conducting compressor outflow to and around said burner section, and a turbine disposed downstream of said burner section, comprising:

an electrostatic probe disposed for response to electrostatic charge in gas adjacent to said burner section;

bias means for providing a bias voltage to said probe; and signal processing means connected for response to said probe, for providing a probe signal in response to each occurrence of significant conductivity of the gas adjacent said probe as indicative of a flow reversal;

characterized by:

the tip of said probe being disposed directly within said dilution air inlet and said signal processing means providing said probe signal in response to the presence of ions directly within said dilution air inlet so as to provide an order of magnitude improvement in the probe signal obtained thereby.

2. Apparatus according to claim 1 for also detecting wear in the engine characterized by:

said signal processing means comprising means for providing said probe signal in response to signals in said probe of or exceeding a first given magnitude, for providing wear monitor signals in response to charged debris in said engine causing signals in said probe of a mangitude which is substantially an order of mangitude lower than said first given magnitude in the absence of said probe signal, and for inhibiting the provision of said wear montior signals in response to the presence of said probe signal.

* * * * *